United States Patent [19]

Knollenberg

[11] Patent Number: 4,594,715
[45] Date of Patent: Jun. 10, 1986

[54] LASER WITH STABILIZED EXTERNAL PASSIVE CAVITY

[75] Inventor: Robert G. Knollenberg, Boulder, Colo.

[73] Assignee: Particle Measuring Systems, Inc., Boulder, Colo.

[21] Appl. No.: 552,689

[22] Filed: Nov. 17, 1983

[51] Int. Cl.$^4$ .............................................. H01S 3/10
[52] U.S. Cl. ...................................... 372/32; 372/26; 372/29
[58] Field of Search ...................... 372/29, 32, 97, 26

[56] References Cited

U.S. PATENT DOCUMENTS

| | | | |
|---|---|---|---|
| 3,406,289 | 10/1968 | Schleusener | 356/335 |
| 3,534,289 | 10/1970 | Clark et al. | 372/26 |
| 3,718,868 | 2/1973 | Pao et al. | 372/32 |
| 3,899,748 | 8/1975 | Bodlaj | 372/32 |

FOREIGN PATENT DOCUMENTS 0039394  3/1977  Japan .................... 372/29

OTHER PUBLICATIONS

Perel et al, "The Effect of Movement of an Additional Mirror on the Intensity Produced by a Gas Laser", *Opt. Spectrosc.*, vol. 37, No. 3, Sep. 1974, pp. 322–324.

Smith, "Stabilized, Single-Frequency Output from a Long Laser Cavity", *IEEE Journal of Quantum Electronics*, vol. QE-1, No. 8, Nov. 1965, pp. 343–348.

*Primary Examiner*—James W. Davie
*Attorney, Agent, or Firm*—O'Rourke & Harris

[57] ABSTRACT

A laser having a stabilized external passive cavity is disclosed, with stabilization being effected by modulation of an external mirror positioned along the laser axis. The laser system includes first, second and third spaced mirrors with the second mirror being an output coupler positioned between the first and third mirrors so that an active cavity is defined between the first and second mirrors and a passive cavity is defined between the second and third mirrors. The active cavity feeds, or pumps, the passive cavity which is stabilized by modulation of the third mirror by movement along the laser axis by linear oscillation to Doppler shift the reflected waves within the passive cavity and thereby produce frequencies that do not interfere with the stable modes of the active cavity. By stabilization of the passive cavity, advantages of an intercavity laser device can be realized without incurring the practical disadvantages of such devices, and results in a laser device that is particularly well suited for particle size measurement.

22 Claims, 14 Drawing Figures

Fig_1a
PRIOR ART

Fig_1b

Fig_3

Fig_4a

*Fig_4b*

*Fig_4c*

Fig_5a

Fig_5b

Fig_5c

Fig_6a

Fig_6b

Fig_6c

LASER WITH STABILIZED EXTERNAL PASSIVE CAVITY

FIELD OF THE INVENTION

This invention relates to a stabilized laser cavity and method of stabilization of the laser cavity, and, more particularly, relates to a gas laser having a stabilized passive cavity and method of stabilizing such a cavity.

BACKGROUND OF THE INVENTION

Laser devices have been heretofore suggested and/or utilized, and such lasers have included gas lasers (see, for example, U.S. Pat. No. 3,428,914) and multi-mode lasers (see, for example, U.S. Pat. No. 4,089,964). In addition, open cavity gas lasers have heretofore been suggested and/or utilized, particularly in the field of particle size measurements (see, for example, U.S. Pat. No. 3,406,289 wherein a device is described for sizing particles using extinction of laser energy). Refinements in extinction particle size measurement utilizing open cavity laser devices were also described by R. G. Knollenberg and B. Schuster in "Detection and Sizing of Small Particles in Open Cavity Gas Laser", Applied Optics, Volume 11, Number 7, November, 1972, pages 1515–1520.

Submicron particle sizing devices utilizing light scattering in an open cavity laser device was first described by R. G. Knollenberg in "An Active Scattering Aerosol Spectrometer", Atmospheric Technology, Number 2, June, 1973, pages 80–81. Refinements have been described by R. G. Knollenberg in "Active Scattering Aerosol Spectrometry", National Bureau of Standards Special Publication 412, issued October 1974, pages 57–64; by R. G. Knollenberg and R. E. Luehr in "Open Cavity Laser 'Active' Scattering Particle Spectrometry from 0.05 to 5 Microns", Fine Particles, Aerosol, Generation Measurement, Sampling and Analysis, Editor Benjamin Y. H. Liu, Academic Press, May, 1975, pages 669–696; by R. G. Knollenberg in "Three New Instruments for Cloud Physics Measurements: The 2-D Spectrometer, the Forward Scattering Spectrometer Probe, and the Active Scattering Aerosol Spectrometer", American Meteorological Society, International Conference on Cloud Physics, July, 1976, pages 554–561; and by R. G. Knollenberg in "The Use of Low Power Lasers in Particle Size Spectrometry", Proceedings of the Society of Photo-Optical Instrumentation Engineers: Practical Applications of Low Power Lasers, Volume 92, Aug. 1976, pages 137–152.

While open cavity gas lasers typically have high Q values (the ratio of the resonant energy density inside a laser cavity to all possible losses is referred to as the "Q" of the cavity), such lasers have presented difficulties in utilization, and this has led to attempts to develop external cavities fed by standard lasers in an attempt to overcome these difficulties. The application of external cavities fed by standard lasers has been heretofore limited, however, due to the low Q values attained, which low Q values have been largely due to the lack of exact phase locking and competition with the cavity having gain.

Attempts have heretofore also been made to frequency stabilize the active cavity of a laser device, and such attempts have included position adjustment of a frequency defining member of the cavity. Such devices are shown, for example, in U.S. Pat. Nos. 3,534,289, 3,718,868 and 3,899,748.

SUMMARY OF THE INVENTION

This invention provides a stabilized laser cavity device and, more particularly a stabilized external passive cavity device. By stabilizing the passive cavity, which is being fed by the active cavity, the advantages of an open cavity laser device is realized without incurring the disadvantages of such devices.

It is therefore an object of this invention to provide an improved laser device and method.

It is another object of this invention to provide an improved laser device having cavity stabilization and a method for achieving cavity stabilization in a laser device.

It is still another object of this invention to provide an improved laser device having a stabilized passive cavity and a method for effecting stabilization of such a cavity.

It is still another object of this invention to provide an improved laser device having an internal cavity feeding an external cavity that is stabilized by sustained movement of a cavity defining member of the external cavity.

It is yet another object of this invention to provide an improved laser device having a passive cavity stabilized by modulation of the external mirror in part defining the passive cavity.

It is yet another object of this invention to provide a method for gas laser stabilization by effecting movement of the external mirror defining in part the passive cavity of the gas laser.

With these and other objects in view, which will become apparent to one skilled in the art as the description proceeds, this invention resides in the novel construction, combination, arrangement of parts and method substantially as hereinafter described and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1b is a graphical presentation of the Doppler broadened Neon line spectrum and laser axial mode structure of a typical HeNe laser as shown in FIG. 1a;

FIG. 4b is a graphical presentation of a typical Doppler spectrum and observed frequency structure produced on a spectrum analyzer for the passive cavity of the device shown in FIG. 4a;

FIG. 5b is a graphical presentation of scan distance versus intensity for the high-order multi-mode laser beam shown in FIG. 5a;

FIG. 5c is a graphical presentation of the Doppler spectrum and high order transverse mode structure produced on a spectrum analyzer for the high order multi-mode laser beam shown in FIG. 5a;

FIG. 6b is a graphical presentation of scan distance versus intensity for the laser beam observed at the external mirror for the laser beam shown in FIG. 6a; and FIG. 6c is a graphical presentation of the frequency structure produced on a spectrum analyzer within the passive cavity of the laser beam observed at the external mirror shown in FIG. 6a.

DESCRIPTION OF THE INVENTION

Lasers are basically resonant cavity devices with permissible lasing frequencies being basically limited to those frequencies which have exact integer number of half-wavelengths of mirror separation since the oscillating laser resonant coherant waves traveling in either direction must be in phase or be extinguished via destructive interference.

This half-integer periodicity requirement limits laser frequencies to discrete, very narrow laser lines (standing waves) the number and spectral range of which are further limited by the plasma's available Doppler-broadened spectrum. These laser lines are referred to as axial modes and have a frequency spacing of $C/2L$ where C is the speed of light and L is the optical path-length of the mirror separation.

Figure 1A:
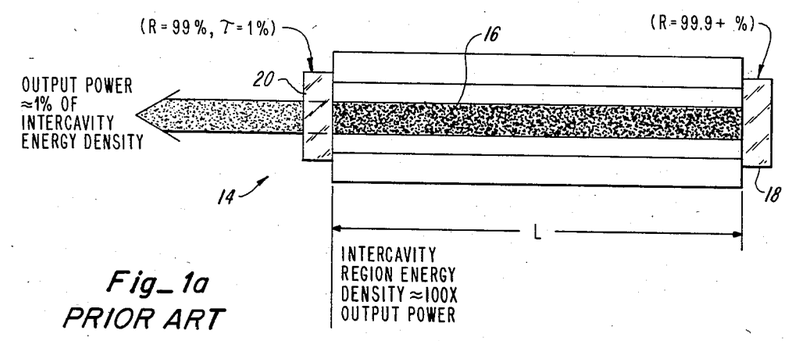
FIG. 1a is a simplified side section view schematic presentation of a typical known gas laser.
Figure 1B:
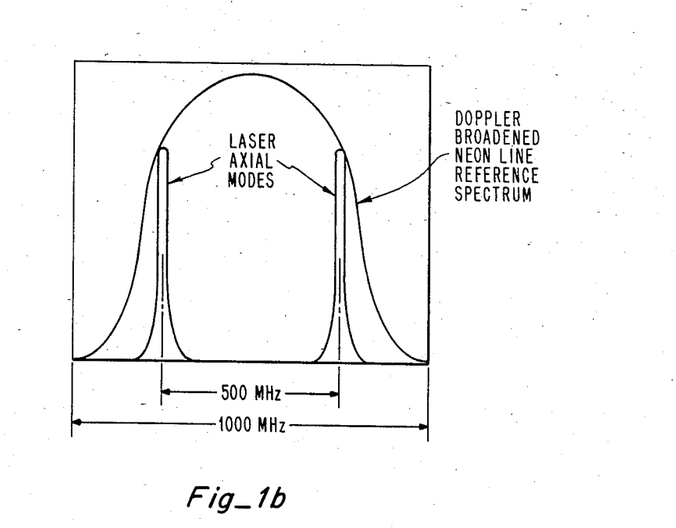

As shown in FIG. 1a, a HeNe laser 14 with a cavity 16 having a length of 30 cm, as defined by the spacing between mirrors 18 and 20, has axial modes spaced at 500 MHz. Since the Doppler spectrum is typically only 1000 MHZ in width for Neon (the lasing atom), only 2 axial modes can be present at any one time in a laser device of this length as indicated in FIG. 1b.

The presence of off-axis paths through the lasing medium permits transverse modes and presents a more complicated line structure than the simple axial mode structure shown in FIG. 1a, by allowing slight path differences from the centerline path represented by L. While such high-order multi-mode operation results in a larger number of permissable laser lines and increases power, noise is added which often results in less useful beam characteristics.

When axial modes are present without the presence of off-axis transverse modes, the laser is said to be operating $TEM_{oo}$. If only one axial mode is present, the laser is said to be operating single frequency.

Another characteristic of HeNe lasers is that the gain is very low ($\sim 1$-5%), and thus the output extracted from the cavity is likewise only a small percentage of the resonating cavity energy density. Typically, only one of the mirrors at the opposite ends of an open cavity laser device is selected as the output coupler and has a transmission of about 1% (reflectivity, $R=99\%$), with the other mirror being manufactured with as high a reflectivity as practical ($R \approx 99.9\% +$).

Since a typical HeNe laser has 99 times more energy density inside its resonant cavity than it can couple as useful output, intercavity use of such lasers have been developed. However, because of the low gain, intercavity losses introduced must likewise be small. One well developed intercavity use has been in the field of particle size measurements (other uses include measurements of extinction and refractivity of gases and reflectivity of optical surfaces).

Figures 2A, 2B:
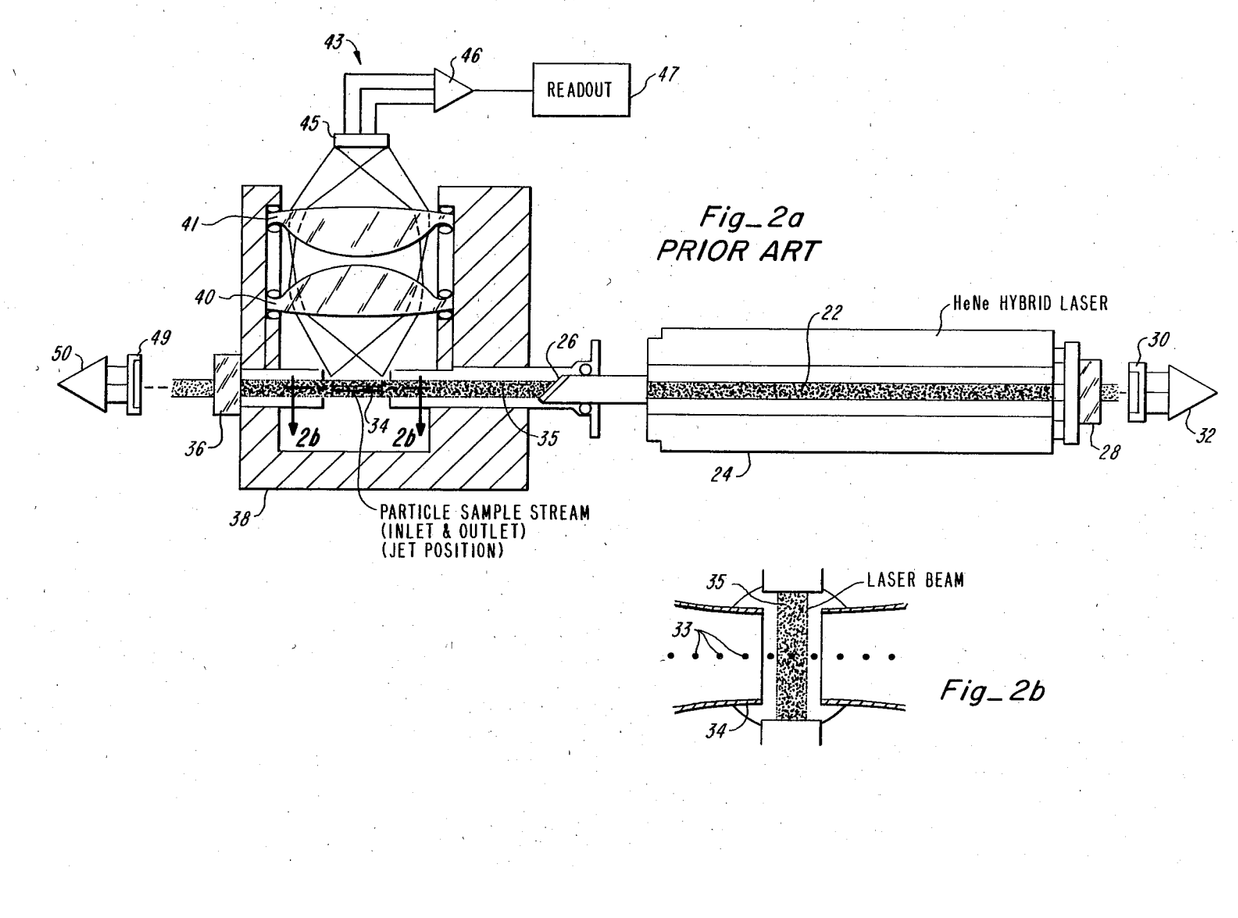
FIG. 2a is a simplified side section view schematic presentation of a typical known arrangement for particle size measurement using an open cavity laser.
FIG. 2b is a partial cross-sectional depiction taken along lines 2b–2b of FIG. 2a illustrating injection of particles to be size measured.

As shown in FIG. 2a, access to laser cavity 22 can be gained by terminating plasma tube 24 at one end with a Brewster's window 26. A curved mirror 28 (with radius $r = 100$ cm, for example) is positioned at the other end of tube 24. A photodetector 30 and preamplifier 32 are conventionally positioned along the laser beam axis outside mirror 28 to provide a measure of relative intensity of illumination.

For particle size measurement, particles 33 to be size measured are injected through jets 34 (as shown best in FIG. 2b so that the particles pass through the laser beam 35 between the Brewster's window 26 and an external laser mirror 36 (with $r=70$ cm, for example). As shown in FIG. 2a, a sample block 38 is positioned above the particle injection area, and block 38 positions light collecting optical elements, such as a pair of lenses 40 and 41, above and close to the particle injection area. A scattering photodetector module 43 is positioned adjacent to block 38, and module 43 includes photodiode 45, conventionally located in the focal plane of lenses 40 and 41, and an amplifier 46. The output from scattering photodetector module 43 is coupled to readout 47 (which may be an oscilloscope, for example). Photodetector 49 and preamplifier 50 may be optionally positioned along the laser beam axis at the other side of mirror 36 to provide the reference measurement as would photodetector 30 and preamplifier 32.

Particles of a few microns and smaller introduce negligible cavity losses requiring that particle detection and sizing be performed utilizing particle light scattering received by the scattering photodetector module 43, while larger particles produce easily measurable losses of energy via monitoring extinction of output power observable at either reference detector 30 or 49. Hence, laser devices such as shown in FIG. 2(a) are useful for particle size measurement. Cavities defined by both mirrors of high reflectivity can be used for particle measurement since high output power is not required. This typically further raises the energy density within the cavity to levels of a watt or more in a tube that would otherwise only be capable of delivering about 1 to 2 milliwatts of output power using an output coupler of 1% transmission. The ratio of the resonant energy density inside a laser cavity to all possible losses is referred to as the "Q" of the cavity as brought out hereinabove. Typical maximum Q values for open cavity HeNe devices are 500 to 1000.

While useful as particle illumination sources, open cavity lasers have nevertheless been found to present problems. For example, because of the high Q values, the exposed internal mirror and Brewster's window surfaces are extremely sensitive to contamination. In addition, as with any laser device, alignment of the mirror system is difficult prior to lasing action. Still another difficulty results from the inability to use high airflows through the cavity since instabilities at high velocity airflow result in equivalent fractional wavelength differences in optical pathlength and this results in random modulation and thus noisy particle size measurements.

Figure 3:
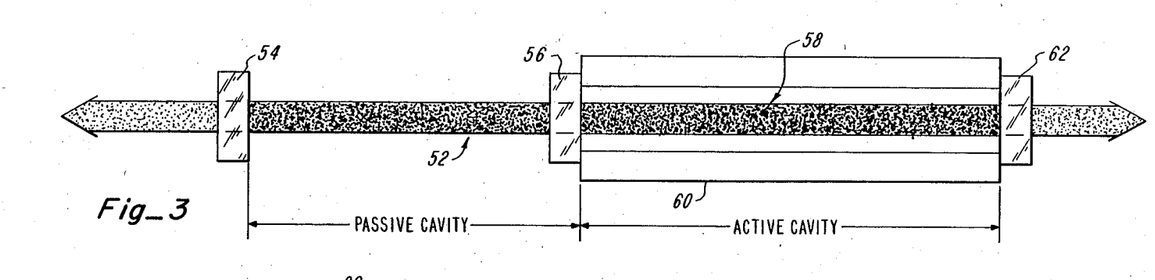
FIG. 3 is a simplified side section view schematic presentation of a typical laser device having an external passive cavity fed by a standard laser.

Difficulties such as set forth hereinabove in using open cavity resonant devices for sizing particles has resulted in attempts to use external cavities fed by standard lasers as indicated typically in FIG. 3. As shown in FIG. 3, a passive cavity 52 is established between external mirror 54 and output coupler mirror 56, while an active cavity 58 is established within tube 60 by mirror 56 at one end and mirror 62 at the opposite end. External mirror 54, output coupler mirror 56 and mirror 62 are beam shaping elements. External mirror 54 is of high reflectivity and this results in the retroreflection of the output power back toward output coupler 56. After many transits, the energy builds up in the external (passive) cavity 52 to such a level that it feeds a certain percentage back into the active gain region 58 between mirrors 56 and 62. This can be observed by monitoring the leakage out of mirror 62 increasing as alignment of mirrors 54 and 56 is approached.

Clearly, there are effectively two cavities (one active with gain and one passive without gain) present which at high Q values have mutual interactions because of the coherence of the laser frequencies. There is also a third active cavity defined between mirrors 54 and 62, but it has a high loss due to the presence of mirror 56. Slight changes in mirror separations, either between mirrors 56 and 62 or mirrors 54 and 56 result in large power fluctuations and these can be observed at mirrors 54 and 62.

The instabilities of arrangements such as set out hereinabove render them undesirable as illumination devices for particle size or related measurements. Regardless of the mirror system employed, the external cavity is limited to Q values of 5 to 10, at best, due to the lack of exact phase locking and competition between the cavities having gain. The energy feedback is only exactly in phase at discrete spacings of mirrors 54 and 56, just as was the case of the above described open cavity laser device. These correspond to strong enhancements observed at mirror 62. Such an arrangement could be stable if operated single frequency and both cavities had precise half integral spacing with respect to the wavelength, or, if both cavities had exactly the same wavelength. Maintenance of such precise spacings, however, is virtually impossible.

This invention stabilizes a passive cavity that is being fed by an active cavity (laser) regardless of cavity length. By stabilizing the passive cavity, Q values of at least a hundred have easily been produced. In fact, the maximum Q value is limited solely by losses in the external cavity in the same manner as the active cavity. Normally, the Q value of the passive and active cavities will be nearly identical.

Figure 4A:
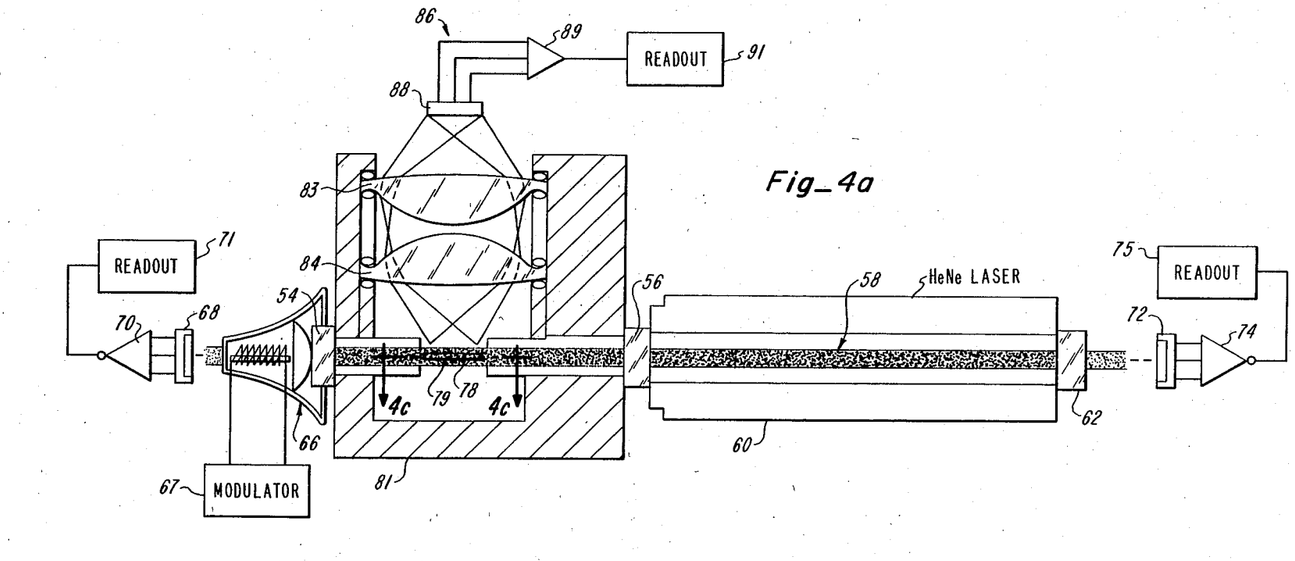
FIG. 4a is a simplified side view section schematic presentation of a laser having an active cavity feeding a passive cavity that is stabilized in accordance with this invention.

Stabilization of the passive cavity is achieved by modulating external mirror 54 along the laser axis by use of suitable linear oscillation. The effect of movement of external mirror 54 is to sufficiently Doppler shift each reflected wave producing a new frequency that will not interfere with the stable axial modes of the active cavity. Subsequent reflections produce additional frequencies until a broad incoherent spectrum results in the passive cavity. An additional result is the destruction of gain within the third cavity defined by mirrors 54 and 62 (see FIG. 4).

FIG. 4(a) illustrates an arrangement wherein sustained movement of external mirror 54 is effected by a common "woofer" audio speaker (voice coil) 66. As shown, mirror 54 is attached at the center of audio speaker 66 (mirrors 54 and 62 are high reflectivity mirrors (<0.1% transmission) while mirror 56 is an output coupler mirror (~1% transmission), and audio speaker 66 is oscillated by modulator 67.

The speaker can be driven by fairly low frequencies (as low as 40 Hz, for example, and experiments have shown that as long as the displacement amplitudes are sufficient to generate velocities of a few tens of centimeters per second, sufficient frequency shifting results to completely decouple the cavities (F>40 Hz with displacement, $\Delta z = 1$ to 5 mm, for example). The translational velocity is the relevant parameter. For example, a 4 inch voice coil can be driven by a 60 Hz (common line AC) frequency at 2 to 3 volts (rms) to provide a few millimeters displacement. This correlates to the appropriate velocity range.

Figure 4B:
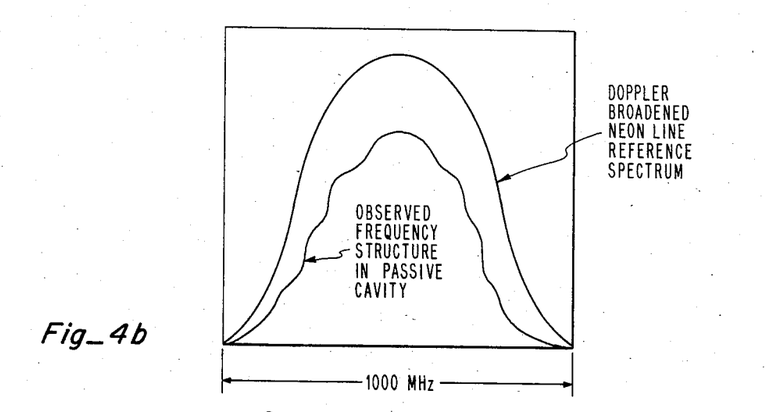

With mirror 54 aligned but voice coil 66 unpowered, the usual instabilities were found to be present and the passive cavity had a fairly low Q value. Both mirrors 54 and 62 showed significant increases of transmission, however, over the unaligned situation. However, once voice coil 66 is powered, the Q value of the passive cavity increased by a factor of 10 or more as evidenced by an increased output from mirror 54 (as measured through photodetector 68 and preamplifier 70 providing an output to readout device 71). Mirror 62, however, showed a reduction in transmission (as measured through photodetector 72 and preamplifier 74 providing an output to readout device 75) to a value close to the unmodulated unaligned condition. The frequency structure at the output of mirror 54 is revealed in FIG. 4b as shown on a spectrum analyzer.

Figure 4C:
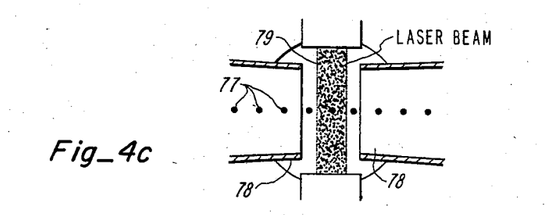
FIG. 4c is a partial cross-sectional depiction taken along lines 4c—4c of FIG. 4a illustrating injection of particles to be size measured.

For particle size measurement, particles 77 to be size measured are injected through jets 78 (as shown in FIG. 4c so that the particles pass through the laser beam 79 in the passive cavity. As shown in FIG. 4a, sample block 81 is positioned above the particle injection area, and block 81 positions light collecting optical elements, such as a pair of lenses 83 and 84, above and close to the particle injection area. A scattering photodetector module 86 is positioned adjacent to block 81, and module 86 includes a photodiode 88, conventionally located in the focal plane of lenses 83 and 84, and an amplifier 89. The output from scattering photodetector module 86 is coupled to readout 91 (which also may be an oscilloscope, for example).

In operation, the laser is caused to generate the laser bean and the external mirror is caused to oscillate with the frequency and amplitude being adjusted to achieve passive cavity stabilization. When utilized for particle size measurements, the particles are then injected into the laser beam in the passive cavity as shown in FIGS. 4a and 4c, and output readings are obtained at readout device 91. The fluctuations in such readings may then be utilized to provide size measurements as is known in the art. A laser device with stabilization of the passive cavity is particularly useful as an illumination device for particle size measurements and such use is nearly ideal. In addition, mirror 54 can also be an output coupler for coupling stabilized passive cavity energy from the device for use externally of the passive cavity.

Figure 5A:
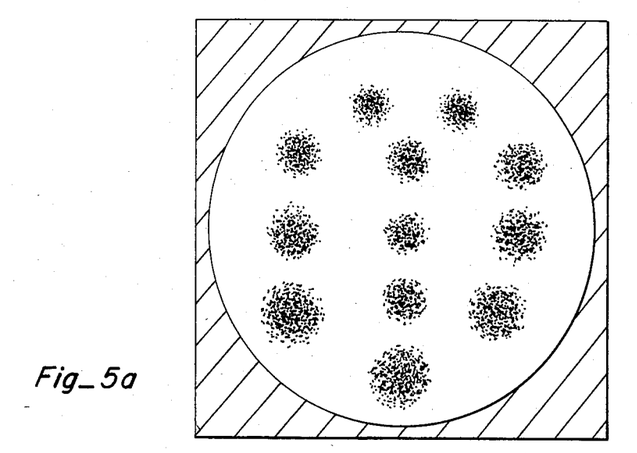
FIG. 5a is an enlarged cross-sectional depiction of a laser beam having a typical complex high-order multi-mode structure that can be stabilized according to this invention.
Figure 5B:
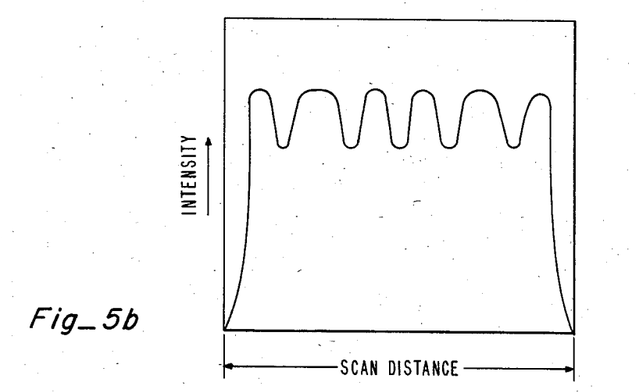
Figure 5C:
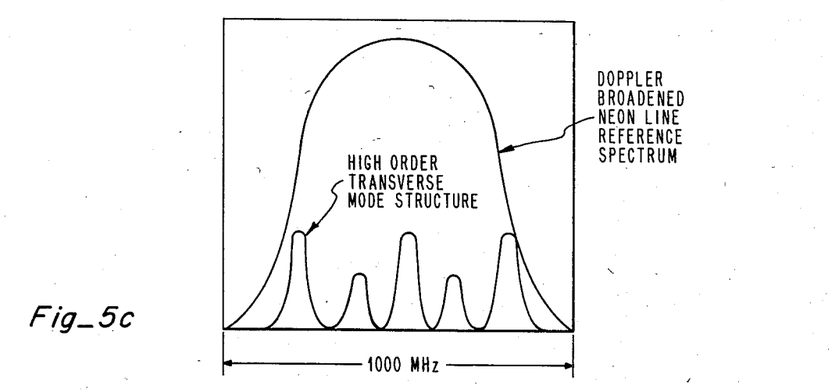
Figure 6A:
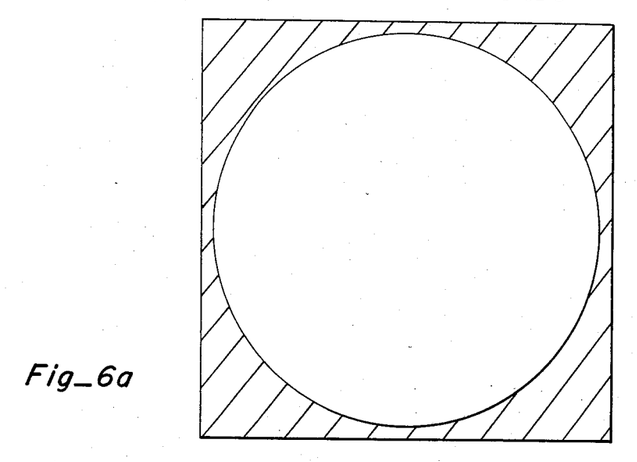
FIG. 6a is an enhanced cross-sectional view of the laser beam as shown in FIG. 5a, observed at the external mirror with stabilization of the passive cavity according to this invention.
Figure 6B:
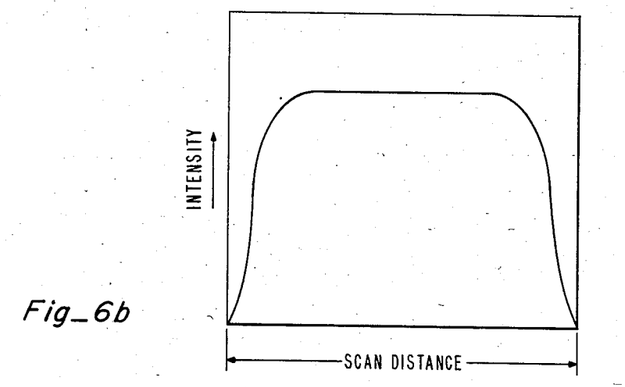
Figure 6C:
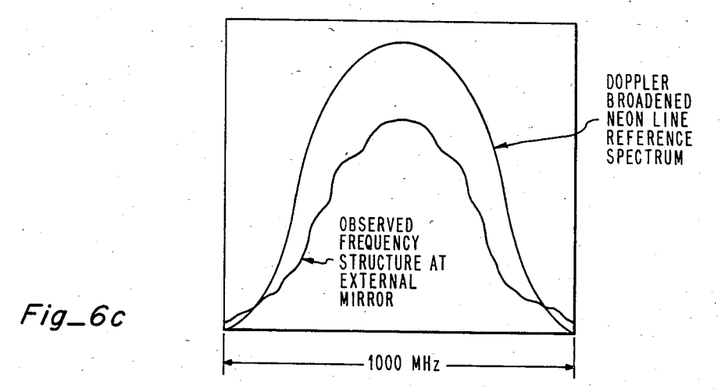

While a HeNe laser device has been specifically mentioned, any laser can be used, even those with complex high-order multi-mode structures such as shown by the laser beam presentation and associated graphs of FIG. 5. When the passive cavity is stabilized according to this invention, the passive cavity exhibits (at mirror 54) little of the self-reproducing complex structure since the frequency and phase-shifting arising from modulation of external mirror 54 mixes many waves of differing frequency and phase content. This is shown by the laser beam presentation and associated graphs of FIG. 6. With respect to the foregoing, a 5 mw multi-mode laser (30 cm cavity) was used to drive a passive cavity with a Q value of 200 producing an energy density of 1 watt. This passive cavity was used as a replacement for a conventional open cavity arrangement, and the same sensitivities were obtained with remarkable improvements in stability and reproducibility.

The maximum Q value of the passive cavity is primarily limited by the quality of the anti-reflection (AR) coating on the transmitting face of the output coupler mirror 56. Mirrors can be fairly easily manufactured with losses of less than 0.01%, but anti-reflection coatings cannot. Furthermore, as previously mentioned, the passive cavity nominally has a Q similar to the active cavity. Consider an active cavity having a 99.99% reflectivity for mirror 62 and 99.81% reflectivity for mirror 56, its total transmission loss is 0.2% and its Q is thus 500 in the absence of additional unknown losses. The output feeds the external cavity which is defined by mirrors 54 and 56. If mirror 56 also has 99.99% reflectivity and the AR coating is perfect, then the passive cavity would also have a Q of 500. However, if the AR coating has 0.1% loss, then the external cavity would lose 0.4% for each round top reflection and lower the Q to 250.

Also, the beam width in the passive cavity can be tailored by constructing output coupler 56 so that the output is focused on mirror 54 or by appropriate choices of radii on the transmitting face. Use of a fairly short radius generates a short focus, and with mirror 54 positioned at the focus, the arrangement is very insensitive to alignment. The displacement of mirror 54 must, however, be small and therefore the modulating frequency increased to achieve sufficient desirable Doppler frequency shifting.

While not specifically shown, modulation of the external mirror of an open cavity device (such as shown in FIG. 2a also results in a filled Doppler envelope of frequencies and reduces annoying effects of exact phase coherence and the resulting standing waves.

As can be appreciated from the foregoing, this invention provides an improved laser device having a passive cavity stabilized by modulation of the external mirror.

What is claimed is:
1. A stabilized laser device, comprising:
    laser beam generating means having an elongated body means terminated at opposite ends by first and second beam shaping elements to form an active cavity, said first beam shaping element transmitting a laser beam within said active cavity in a predetermined direction from said active cavity;
    an external beam shaping element spaced from said active cavity and positioned in the path of said laser beam transmitted from said active cavity, said external beam shaping element and said first beam shaping element defining a passive cavity therebetween; and
    modulating means connected with said external beam shaping element to oscillate said external beam shaping element to thereby stabilize said passive cavity.

2. The device of claim 1 wherein said beam shaping elements are mirrors.

3. The device of claim 1 wherein said external beam shaping element is an output coupler for coupling stabilized passive cavity energy from the device for use externally of said passive cavity.

4. The device of claim 1 wherein said device includes means for injecting particles into said laser beam at said passive cavity, and wherein said device also includes means for determining particle size measurement by detecting laser output.

5. The device of claim 1 wherein said modulating means includes oscillator means.

6. The device of claim 5 wherein said oscillator means operates at a frequency of about 60 Hz.

7. The device of claim 1 wherein said modulating means includes a voice coil having said external mirror means connected thereto to effect movement of said external beam shaping element.

8. The device of claim 1 wherein said modulating means oscillates said external beam shaping element such that the displacement amplitudes generate velocities of a few tens of centimeters per second.

9. The device of claim 8 wherein said generated displacement amplitudes completely decouple the active and passive cavities.

10. A stabilized gas laser device, comprising:
    laser beam generating means having a plasma tube terminated at opposite ends by first and second mirror means to form an active cavity, said first mirror means acting as an output coupler for transmitting a laser beam within said active cavity from said cavity in an axial direction with respect to said tube;
    third mirror means positioned external to said active cavity and in the path of said laser beam transmitted from said active cavity, said first and third mirror means forming a passive cavity coaxial with and adjacent to said active cavity; and
    modulating means including oscillator means and audio speaker means connected with said third mirror means and said oscillator means to effect oscillation of said third mirror means to thereby stabilize said passive cavity.

11. The device of claim 10 wherein said passive cavity defined by said first and third mirror means produces Q values, when modulated by said modulating means, increased by at least a factor of ten relative to said device when not modulated by said modulating means.

12. The device of claim 11 wherein said produced Q values are in excess of a hundred.

13. The device of claim 10 wherein said oscillator means is a linear oscillator.

14. The device of claim 10 wherein said active cavity has predetermined stable axial modes, and wherein said oscillator means causes oscillation of said external mirror means along the laser axis to sufficiently modulate said external mirror to produce Doppler shifted frequencies that do not interfere with said stable axial modes of the active cavity.

15. The device of claim 14 wherein said oscillator means operates at a frequency of about 60 Hz, with a voltage of between about two and three volts driving said speaker means.

16. The device of claim 10 wherein said laser device has a high-order multi-mode structure, and wherein said modulating means causes stabilization of said passive cavity by further randomizing said high-order multimode structure within said passive cavity.

17. A method for stabilizing a laser, said method comprising:
   generating a laser beam within an active cavity of a laser device;
   transmitting said laser beam from said active cavity in a predetermined direction;
   positioning an external reflective device in the path of said transmitted laser beam to reflect the same with said reflective device being positioned to define a passive cavity between the reflective device and the active cavity; and
   effective modulation of the reflective device by oscillation of said reflective device to stabilize the passive cavity of the laser.

18. The method of claim 17 wherein said oscillation of said reflective device is in a direction substantially parallel to said laser beam and of a magnitude to sufficiently modulate said reflective means to produce frequencies that do not interfere with the stable axial modes of the active cavity.

19. The method of claim 17 wherein said oscillator of said reflective device operates at a low frequency.

20. The method of claim 17 wherein said oscillation of said reflective device is linear.

21. The method of claim 17 wherein said reflective device is oscillated such that displacement amplitudes generate velocites of a few tens of centimeters per second.

22. The method of claim 21 wherein said generated displacement amplitudes completely decouple the active and passive cavities.

* * * * *